United States Patent [19]

Shaw

[11] Patent Number: 4,978,796
[45] Date of Patent: Dec. 18, 1990

[54] N-ALKYLPYRROLIDONE SOLVENTS FOR PREPARATION OF AROMATIC THIOLS

[75] Inventor: James E. Shaw, Bartlesville, Okla.

[73] Assignee: Phillips Petroleum Company, Barlesville, Okla.

[21] Appl. No.: 473,015

[22] Filed: Jan. 31, 1990

[51] Int. Cl.$^5$ ........................................... C07C 319/02
[52] U.S. Cl. ..................................................... 568/68
[58] Field of Search .................................... 568/68, 60

[56] References Cited

U.S. PATENT DOCUMENTS 3,374,274  3/1968  Spainhour .............................. 568/68
3,415,889  12/1968  Louthan ................................ 568/68
4,209,469  6/1980  Thies et al. ........................... 568/68

OTHER PUBLICATIONS

Testaferri, L., "Simple Syntheses of Aryl Alkyl Thioethers and of Aromatic Thiols From Unactivated Aryl Halides and Efficient Methods for Selective Dealkylation of Aryl Alkyl Ethers and Thioethers", 1983, p. 752.

Maiolo, F., "Fragmentation of Aryl Alkyl Sulfides, A Simple, One—Pot Synthesis of Polymercaptobenzenes from Polychlorobenzenes", 1980, p. 3070.

Testaferri, L., "A Convenient Synthesis of Aromatic Thiols From Unactivated Aryl Halides", 1980, vol. 21, p. 3099.

Primary Examiner—Mary E. Ceperley
Attorney, Agent, or Firm—Archie L. Robbins

[57] ABSTRACT

A process using N-alkylpyrrolidone solvents, such as N-methylpyrrolidone (NMP), for the preparation of aromatic thiols, from the reaction of aryl halides and alkali metal alkanethiolate. This process produces aromatic thiols in higher yields and purity.

11 Claims, No Drawings

N-ALKYLPYRROLIDONE SOLVENTS FOR PREPARATION OF AROMATIC THIOLS

BACKGROUND OF INVENTION

This invention relates to the preparation of aromatic thiols.

Aromatic thiols such as thiophenols are well known compounds with a variety of commercial uses. These compounds are used in pharmaceutical synthesis, as a rubber plasticizer, in the reclaiming of rubber, and in the manufacture of insecticides and agro-chemicals.

The preparation of aromatic thiols is also well known in the art. Spainhour (U.S. Pat. No. 3,374,274) teaches preparing aromatic thiols and sulfides by reacting a nuclear monohalo substituted compound with an excess of an alkali metal sulfide. Louthan (U.S. Pat. No. 3,415,889) discloses the preparation of aromatic heterocyclic thiols by reacting an alkali metal sulfide with polyhalo compound(s), in the presence of a polar organic compound solvent. Furthermore, Thies (U.S. Pat. No. 4,209,469) teaches the production of aryl thiol by hydrogenating an aryl sulfur chloride in a protic or aprotic solvent in the presence of platinum as a catalyst. Of more relevance to the present invention is the disclosure by Testaferri et al. (Syntheses 1983 at page 752) showing the preparation of aromatic thiols by reacting an aryl halide with sodium alkanethiolate using N,N-dimethylformamide (DMF) as a solvent.

This invention differs from the Testaferri et al. method in, at least, the following respects. First, unlike the Testaferri et al. method, this invention works well when alkyl substituted aryl halides are used. Second, in this invention, the undesired loss of sodium alkanethiolate, an essential intermediate reactant, does not occur. Third, the rate of the reaction is significantly increased by the method of this invention.

In a nutshell, the present invention represents an improved, simple and inexpensive "one pot reaction" process for the preparation of aromatic thiols in the desired purity and yield.

SUMMARY OF INVENTION

It is the general object of this invention to provide a significantly new and improved process for the production of aromatic thiols of the requisite purity and yield.

A further object of this invention is to achieve high conversion rate in the production of aromatic thiols from aryl halides and alkali metal alkanethiolate.

In accordance with this invention, aromatic thiols are produced by contacting an aryl halide with an alkali metal alkanethiolate in the presence of an N-alkylpyrrolidone solvent.

DETAILED DESCRIPTION OF THE INVENTION

The present invention is based on the discovery that an alkylpyrrolidone such as N-methylpyrrolidone (NMP) is a superior solvent to N,N-dimethylformamide (DMF) in the reaction of aryl halide and an alkali metal alkanethiolate in the process for the preparation of aromatic thiols.

The aryl halides useful in this invention can be represented by the chemical formula R'ArX where:

R' = H, alkyl, aryl, halo (chloro, bromo, iodo, fluoro), amino, alkylamino, alkoxy, alkylthio (alkylmercapto).

Ar = any aromatic ring such as benzene, napthalene, anthracene, phenanthrene, indene, fluorene, pyridine, quinoline, pyrrole, indole, thiophene, benzothiophene, furan, benzofuran, and the like.

X = halogens, preferably chlorine.

The alkali metal alkanethiolates useful in this invention can be represented by the chemical formula RSM where:

R = a primary or secondary alkyl group such as methyl, n-propyl, ethyl, isopropyl and the like.

M = an alkali metal (Li, Rb, Na, Cs, or k).

Solvents useful in this invention are N-alkylpyrrolidones solvents, such as N-ethyl, N-propyl, and other $C_2$–$C_8$ N-alkylpyrrolidones. However, N-methylpyrrolidone (NMP), is preferred.

The alkali metal alkanethiolates useful in this invention, can either be obtained commercially or synthesized in the laboratory. Laboratory synthesis can usually be accomplished by reacting an alkyl mercaptan, preferably primary or secondary alkyl mercaptans, with an alkali metal hydroxide or alkali metal hydride in the presence of NMP. In one specific embodiment of this invention, an alkyl mercaptan (n-propyl mercaptan) is reacted with an alkali metal hydroxide (NaOH) in a reaction vessel. This reaction can be performed in the range of 1:1 to 1.5:1 molar ratio of the reactants, although the preferred ratio is a 1:1 molar ratio. The reactants are stirred and heated to facilitate dissolution of the solid sodium hydroxide. The reaction is conducted at ambient pressure. This reaction is further facilitated by the addition of N-methylpyrrolidone (NMP) to the reaction vessel, and is essentially a neutralization reaction that results in the formation of the alkali metal salt of the mercaptan. It is represented by the chemical equation below:

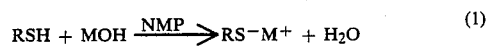

$$RSH + MOH \xrightarrow{NMP} RS^-M^+ + H_2O \quad (1)$$

where R is a primary or secondary alkyl group such as methyl, n-propyl, ethyl, isopropyl, etc. and M is an alkali metal (Li, Rb, Na, Cs, K,).

The water formed in the above reaction is removed by addition of toluene to the reaction vessel, followed by heating the mixture to reflux. It is desirable to remove the water, because its presence tends to slow subsequent reactions probably by associating with the nucleophile. The process of water removal can also be accomplished by distillation or similar methods, or by the addition of any solvent that will form an azeotrope with water.

Use of the alkali metal hydride does not result in water formation and avoids using toluene and/or other water removing agents or techniques. This reaction can be represented by the equation below:

$$RSH + MH \xrightarrow{NMP} RSM^+ + H_2 \uparrow \quad (2)$$

where R and M are the same as in equation (2) above.

Typically, this invention is carried out by contacting at least one aryl halide and at least one alkali metal alkanethiolate in the presence of an N-alkylpyrrolidone solvent. Such contacting can employ any method known in the art. The range of reactants is generally from about 2:1 to about 10:1 molar ratio of the alkali metal alkanethiolate to aryl halide respectively, with a preferred ratio of 4:1 molar ratio. Sufficient pyrrolidone, in a broad ratio of 45:5, but preferably in the ratio of 15:1 molar ratio of the aryl halide is needed for this invention's reactions. The reaction can be suitably carried out at a temperature generally in the range of from about 100° C. to about 250° C., although a temperature above 180° C. is preferred. The reaction can be conducted at any suitable pressure, but is preferably conducted at ambient pressure. The reaction can be conducted for any period of time necessary to achieve the desired completion of the reaction, such as for example, about 20 hours.

The completed reaction results in the formation of an aromatic thiol and a di-n-alkyl sulfide. These products can then be collected, separated, and analyzed by using conventional methods known in the art.

In one embodiment of this invention, an alkyl substituted aryl halide, (4-chlorotoluene) can be reacted with an alkali metal alkanethiolate synthesized as previously disclosed. The reaction conditions can be within the ranges recited above and the methods disclosed in the preceding paragraphs can be employed.

Two distinct chemical reactions occur. First, the aryl halide (alkyl substituted) reacts with dissociated alkali metal salt of mercaptan to form an aryl alkyl sulfide, which in turn reacts with the same mercaptan salt to form an aromatic thiol (e.g. sodium thiophenolate) and a di-n-alkyl sulfide. These reactions can be represented by the chemical equations shown below:

M=alkali metal (Li, Na, K, Rb, Cs)
R'=H, alkyl, aryl, halo (chloro, bromo, iodo, fluoro), amino, alkylamino, alkoxy, alkylthio (alkylmercapto).
X=Halogens, preferably Cl.
Ar=any aromatic ring such as benzene, napthalene, anthracene, phenanthrene, indene, fluorene, pyridine, quinoline, pyrrole, indole, thiophene, benzothiophene, furan, benzofuran, and the like;
R=primary or secondary alkyl group such as methyl, ethyl, n-propyl, isopropyl, n-butyl, isobutyl, sec-butyl, and the like.

After cooling to room temperature, a mineral acid, such as hydrochloric acid can be added to the flask in order to form the free thiophenol. Following this, a sufficient quantity of water can be added so as to dissolve the alkali metal salt formed by the proceeding neutralization reaction. Extraction can be effected by addition of ethyl ether, although other suitable organic solvents are likewise useful. The thiophenol, dialkyl sulfide, and any unreacted alkyl mercaptan mix into the organic layer, while the sodium chloride and NMP remain in the aqueous layer. The organic layer can then be washed with water, dried with anhydrous sodium sulfate, and evaporated under reduced pressure. This leaves only the thiophenol and dialkyl sulfide which can be separated and analyzed by gas chromotography.

COMPARATIVE RUN 1

Preparation of p-thiocresol using sodium n-butanethiolate in N,N-dimethylacetamide (DMA)

To a liter 3-neck flask equipped with $N_2$ inlet, thermowell, magnetic stir bar, and Dean Stark trap with condenser was added 300 mls DMA, 32 g (0.80 mol) sodium hydroxide and 72.4 g (86 ml, 0.80 mol) n-butyl mercaptan. The mixture was stirred and heated slightly until the NaOH dissolved. Then 125 ml toluene was added and the mixture was heated to reflux with water being removed by the Dean Stark trap. After all the water (approximately 14 mls) was removed, the toluene (125 ml) was distilled out. An extra 10 ml of liquid was distilled out to ensure that the toluene was gone. The reaction flask was allowed to cool almost to room temperature. The Dean Stark trap was removed, but the condenser was retained. Then 25.3 g (24 ml, 0.20 mol) 4-chlorotoluene was added and the solution was refluxed overnight (20 hours). The solution was cooled to room temperature. A solution of 75 ml concentrated hydrochloric acid and 75 mls water was added slowly with stirring and cooling so the mixture had a pH of 3. After addition of an extra 150 ml of water, the mixture was extracted with 300 ml ethyl ether. The aqueous layer was extracted a second time with 150 ml ethyl ether. The combined ether extract was washed with three 50 ml portions of water, dried with anhydrous sodium sulfate, and evaporated under reduced pressure to give 46.7 g of liquid. GC analysis (OV-101 column) of the liquid showed that it contained 36.1% unreacted 4-chlorotoluene and only 8.4% p-thiocresol. The yield of p-thiocresol was 16%. The amount of unreacted 4-chlorotoluene was 67% of initial 4-chlorotoluene. Additionally, an undesirable reaction between sodium n-butanethiolate and DMA resulted in the release of dimethylamine. This probably explains the low yield of only 16% and low conversion of 4-chlorotoluene.

This example illustrates that DMA is not an ideal solvent medium for the nucleophillic displacement of halide by thiolate ion.

COMPARATIVE RUN 2

Preparation of p-thiocresol using sodium n-butanethiolate in DMF

To a 1000 ml 3-neck flash equipped with Dean Stark trap, condenser, $N_2$ inlet, and magnetic stir bar was added 200 ml DMF, 12.0 g (0.30 mol) sodium hydroxide, and 21.0 g (25.0 ml, 0.34 mol.) ethyl mercaptan. The mixture was stirred at room temperature until all the sodium hydroxide dissolved. Then 90 ml toluene was added and the mixture was heated to reflux with water being removed by the Dean Stark trap. After all the water was removed, the toluene (90 mls) was distilled out. An extra 30 mls of liquid was distilled out to be sure toluene was gone. The reaction flask was allowed to cool almost to room temperature. The Dean Stark trap was removed but the condenser was retained. Then 5.04 g (0.04 mol) 4-chlorotoluene was added and the solution was refluxed overnight (20 hrs.). It was again apparent that some DMF was reacting with sodium n-butanethiolate since dimethylamine was given off. The solution was cooled to room temperature. A 3M aqueous HCl solution was added slowly with stirring and cooling so the mixture had a pH of 3. After addition of an extra 100 mls water, the mixture was extracted twice with 200 ml portions of ethyl ether. The combined ether extract was washed with three 40 ml portions of water, dried with anhydrous sodium sulfate and evaporated under reduced pressure to give 6.15 g liquid. GC analysis (OV-101) of the liquid showed that it contained 14.6% p-thiocresol. The yield of p-thiocresol was 18%.

This example illustrates that DMF is not an ideal solvent for nucleophilic substitutes of halide by thiolate ion.

INVENTIVE RUN 1

Preparation of p-thiocresol using sodium n-butanethiolate

To a liter 3-neck flask equipped with N₂ inlet, thermowell, magnetic stir bar, and Dean Stark trap with condenser was added 300 mls NMP, 32 g (0.80 mol) sodium hydroxide, and 72.4 g (86 ml, 0.80 mol) n-butyl mercaptan. The mixture was stirred and heated slightly until the NaOH dissolved. The 125 ml toluene was added and the mixture was heated to reflux with water being removed by the Dean Stark trap. After all the water (approximately 14 mls) was removed, the toluene (125 ml) was distilled out. An extra 10 ml of liquid was distilled out to ensure that the toluene was gone. The reaction flask was allowed to cool almost to room temperature. The Dean Stark trap was removed, but the condenser was retained. Then 25.3 g (24 ml, 0.20 mol) 4-chlorotoluene was added and the solution was refluxed (approximately 186° C.) overnight (20 hours). The solution was cooled to room temperature. A solution of 75 ml concentrated hydrochloric acid and 75 ml water was added slowly with stirring and cooling so the mixture was extracted with 300 ml ethyl ether. The aqueous layer was extracted a second time with 150 mls ethyl ether. The combined ether extract was washed with three 50 ml portions of water, dried with anhydrous sodium sulfate, and evaporated under reduced pressure to give 81.4 g of liquid. GC analysis (OV-101 column) of the liquid showed that it contained 27.5% p-thiocresol and 37.9% n-butyl sulfide. The yield of p-thiocresol was 90%.

This example demonstrates that NMP is a superior solvent to both both DMA and DMF in nucleophilic substitution of halide by thiolate ion. It greatly improves the yield of product.

INVENTIVE RUN 2

Preparation of p-Thiocresol using sodium n-propanethiolate

To a 3 liter 3-neck flask equipped with N₂ inlet, thermowell, magnetic stir bar, and Dean Stark trap with condenser was added 900 mls NMP, 96 g (2.4 mol) sodium hydroxide, and 183 g (218 ml, 2.4 mol) n-propyl mercaptan. The mixture was stirred and heated slightly until the NaOH dissolved. Then 375 mls toluene was added and the mixture was heated to reflux with water being removed by the Dean Stark trap. After the water (approximately 45 ml) was removed, the toluene (375 ml) was distilled out. An extra 25 ml of liquid was distilled out to be sure toluene was gone. The reaction flask was allowed to cool almost to room temperature. The Dean Stark trap was removed, but the condenser was retained. Then 76.0 g (72 ml, 0.60 mol) 4-chlorotoluene was added and the solution was refluxed (approximately 186° C.) overnight (20 hours). The solution was cooled to room temperature. A solution of 225 ml concentrated hydrochloric acid and 225 ml water was added slowly with stirring and cooling so the mixture had a pH of 3. After addition of an extra 450 ml water, the mixture was extracted with 900 ml ethyl ether. The aqueous layer was extracted a second time with 450 mls ethyl ether. The combined ether extract was washed with three 150 ml portions of water, dried with anhydrous sodium sulfate, and evaporated under reduced pressure to give 172 g of liquid. GC analysis (OV-101 column) of the liquid showed that it contained 41.6% p-thiocresol and 30.7% di-n-propyl sulfide. The yield of p-thiocresol was 96%.

The reaction products from two reactions of this scale were combined and fractionally distilled (2:1 reflux ratio) on a column containing high efficiency stainless steel packing. The distilled yield of p-thiocresol of 96% purity was 87%.

This example again, demonstrates that NMP is an excellent solvent for the preparation of thiophenols by nucleophilic substitution of halide by a lower alkylthiolate ion.

INVENTIVE RUN 3

Preparation of o-thiocresol using sodium n-butanethiolate

This reaction was carried out the same way as described in Inventive Run 1 with the exception that 2-chlorotoluene was used as reactant and the amount of 2-chlorotoluene used was 25.3 g (23.4 ml, 0.20 mol). Work-up gave 67.2 g liquid product. GC analysis (OV-1-1 column) of the liquid showed the liquid contained 35.3% o-thiocresol and 44.0% di-n-butyl sulfide. The yield of o-thiocresol was 96%.

This example shows that the invention works well not only for p-thiocresol but also for other isomers such as o-thiocresol.

While this invention has been described in detail for the purpose of illustration, it is not to be construed as limited thereby but is intended to cover all changes and modifications within the spirit and scope thereof.

That which is claimed is:

1. A process for the preparation of aromatic thiols comprising contacting an aryl halide with an alkali metal alkanethiolate in the presence of N-alkylpyrrolidone and thereafter adding acid to form said thiol.

2. A process in accordance with claim 1 wherein said N-alkylpyrrolidone is N-methylpyrrolidone.

3. A process in accordance with claim 1 wherein said aryl halide is an alkyl substituted aryl halide.

4. A process in accordance with claim 1 wherein said alkali metal alkanethiolate is derived from at least one alkyl mercaptan.

5. A process in accordance with claim 4 wherein said alkyl mercaptan is selected from primary and secondary alkyl mercaptans.

6. A process in accordance with claim 1 wherein said contacting is carried out at a temperature range between 100° C. to 250° C.

7. A process in accordance with claim 6 wherein said temperature is within the range of 180° C. to 200° C.

8. A process in accordance with claim 3 wherein said alkali metal alkanethiolate is synthesized by reacting an alkyl mercaptan with an alkali metal hydride.

9. A process in accordance with claim 4 wherein said alkali metal alkanethiolate is synthesized by reacting on alkyl mercaptan with an alkali metal hydroxide.

10. A process for the preparation of p-thiocresol comprising contacting 4-chlorotoluene with an alkanethiolate selected from the group consisting of sodium n-butanethiolate and sodium n-propanethiolate in the presence of N-methylpyrrolidone at a temperature range of 180° C. to 200° C. and thereafter adding hydrochloric acid to form said p-thiocresol.

11. A process for the preparation of o-thiocresol comprising contacting 2-chlorotoluene with sodium n-propanethiolate in the presence of N-methylpyrrolidone at a temperature in the range of 180° C. to 200° C. and thereafter adding hydrochloric acid to form said o-thiocresol.

* * * * *